United States Patent [19]

Kish

[11] E Re. 30,216

[45] Reissued Feb. 19, 1980

[54] TOBACCO SUCKER CONTROL AGENT AND METHOD

[75] Inventor: Calman J. Kish, North Plainfield, N.J.

[73] Assignee: Fairmount Chemical Company, Inc., Newark, N.J.

[21] Appl. No.: 923,820

[22] Filed: Jul. 12, 1978

Related U.S. Patent Documents

Reissue of:

[64] Patent No.: 4,077,796
Issued: Mar. 7, 1978
Appl. No.: 744,649
Filed: Nov. 24, 1976

U.S. Applications:

[63] Continuation-in-part of Ser. No. 549,815, Feb. 14, 1975, abandoned.

[51] Int. Cl.[2] ..... A01N 5/00

[52] U.S. Cl. ..... 71/78; 71/92; 71/122

[58] Field of Search ..... 71/78, 92, 122

[56] References Cited

U.S. PATENT DOCUMENTS

| | | | |
|---|---|---|---|
| 2,614,916 | 10/1952 | Hoffmann | 71/92 |
| 2,805,926 | 9/1957 | Schoene et al. | 71/92 |
| 3,193,373 | 7/1965 | Parups | 71/78 |
| 3,438,765 | 4/1969 | Tso et al. | 71/78 |
| 3,556,763 | 1/1971 | Gower et al. | 71/78 |
| 3,697,250 | 10/1972 | Young et al. | 71/78 |
| 3,824,094 | 7/1974 | Tso et al. | 71/78 |
| 3,900,307 | 8/1975 | Abramitis | 71/122 |

FOREIGN PATENT DOCUMENTS

| | | | |
|---|---|---|---|
| 46-273 | 6/1971 | Japan | 71/78 |

*Primary Examiner*—Glennon H. Hollrah
*Attorney, Agent, or Firm*—Darby & Darby

[57] ABSTRACT

This invention pertains to a method for controlling the growth of axillary buds or suckers in tobacco plants by application of a homogenized liquid mixture of a saturated fatty alcohol selected from the group consisting of $C_6$ to $C_{18}$ saturated fatty alcohols and a salt of 1,2-dihydro-pyridazine, 3,6-dione to the tobacco plant after the tobacco flower has been removed.

17 Claims, No Drawings

TOBACCO SUCKER CONTROL AGENT AND METHOD

Matter enclosed in heavy brackets [ ] appears in the original patent but forms no part of this reissue specification; matter printed in italics indicates the additions made by reissue.

This application is a continuation-in-part of my copending application Ser. No. 549,815 filed Feb. 14, 1975 now abandoned.

The growing of tobacco involves the breaking off or topping of the flower head when the buds begin to flower. The plant, having been shorn of its reproductive power, attempts to propagate by putting out axillary buds or suckers. Suckers are sprouts or shoots which form at the axis of the main stalk and each tobacco leaf. If not eliminated or controlled, the suckers proliferate and grow thereby draining effective plant nutrients from the tobacco leaves and hindering their growth to optimum size.

In the past, those engaged in tobacco production have removed suckers by hand; however, since there can be as many as 20 suckers per plant and 8,700 plants per acre, this method was found to be far too time consuming and expensive. Another means for controlling sucker proliferation comprises application of a small amount of mineral oil to each sucker. Although this treatment eliminates sucker growth, it requires the exercise of great care since the mineral oil will cause severe damage if brought into contact with the leaf, as opposed to the axillary bud or sucker.

A later development in sucker removal required topping the tobacco plant, removing the few small suckers by hand, and then a few days later spraying the plants mechanically with a water solution containing three pounds of maleic hydrazide per acre of tobacco plants. The maleic hydrazide is systemically absorbed into the tobacco plant and prevents the formation of suckers by inhibiting cellular subdivision while at the same time permitting the established leaves to grow. While relatively effective, it usually requires two applications of maleic hydrazide after topping (at intervals of about a week or more) in order to eliminate substantially all of the suckers from a field of growing tobacco. The quantity of maleic hydrazide used on a tobacco crop must be carefully controlled since application of an excessive amount (of maleic hydrazide or its derivatives) yields an undesirable oily tobacco leaf which contains large amounts of objectionable maleic hydrazide residue.

More recently it was found that $C_6$–$C_{18}$ saturated fatty alcohols can be applied to tobacco plants to kill tobacco suckers on contact. However, the application of fatty alcohols alone does not effectively control tobacco suckers on tobacco plants. This is attributable to their being contact-type sucker control agents which quickly drain off the plant thereby terminating their effectiveness as a sucker control chemical. Thus, suckers appearing after the alcohols have drained off are not affected and will continue to mature.

The current agricultural practice is to apply about 12 to 15 pounds per acre of tobacco plants (approximately 1.25 cc per plant) of fatty alcohols as a contact sucker killer within a day or so after the plant is topped, followed about five days later with a second fatty alcohol treatment. A week or so thereafter, approximately 2.4 to 3.0 pounds per acre (approximately 170 milligrams per plant) of maleic hydrazide (in the form of a solution of a salt) is applied to the tobacco plants as a systemic sucker control agent.

While the sequential application of saturated fatty alcohols and maleic hydrazide salt is a relatively effective treatment for inhibiting sucker proliferation, it requires at least two or more spraying operations and results in undesirably high levels of maleic hydrazide residue in the harvested tobacco leaves.

Maleic hydrazide may produce adverse ecological effects when applied in the high dosages heretofore employed in treating tobacco plants. Moreover, application of high dosages of maleic hydrazide also tends to reduce the quantity of useable tobacco leaves and to yield a lower quality leaf. It is accordingly a principal objective in the field of tobacco agricultural research to find an effective sucker control technique which would afford a reduction in the amount of maleic hydrazide used on tobacco and reduce the level of maleic hydrazide residues in the mature tobacco leaf.

With the advent of mechanical harvesting equipment, a sucker control treatment which does not eliminate at least about 90% of the sucker growth is considered deficient. At the time of topping, the young tobacco leaves are still extremely tender, and application of maleic hydrazide in effective amounts to control these undesirable shoots was found to cause irreparable leaf damage.

It has now been unexpectedly discovered that tobacco sucker growth and proliferation can in most cases be controlled with a single application shortly after topping of an aqueous homogenized mixture containing a saturated $C_6$ to $C_{18}$ fatty alcohol (or a mixture thereof) and a salt of 1,2-dihydro-pyridazine-3,6-dione, the latter being obtained by preparing the salts of the reaction product of maleic anhydride and hydrazine.

The fatty alcohol and maleic hydrazide derivative are applied in amounts substantially lower than those heretofore considered to be the minimum effective dosages. Since the aqueous solutions of the invention can be applied in a single spraying operation in most cases, instead of the presently employed method which requires several sequential applications of sucker inhibition chemicals over an extended period of time, the amount of labor required is considerably reduced. A further advantage provided by the invention is to reduce the overall quantity of chemicals applied to the tobacco and in particular to reduce the amount of undesirable maleic hydrazide residues in the harvested and marketed tobacco leaves. The foregoing and other advantages and aspects of the present invention will be apparent upon consideration of the following description.

The objective of the present invention is achieved by treating topped tobacco plants with a homogeneous, aqueous solution containing a saturated $C_6$ to $C_{18}$ fatty alcohol and a salt of 1,2-dihydro-pyridazine-3,6-dione. The solution contains from about 5 to about 25% by weight of the pyridazine salt and from about 10% to about 40% by weight of the saturated fatty alcohol constituent. However, the proportion of ingredients in the solution is not critical and may be varied depending upon the number of plants to be treated so as to deposit the proper quantity of chemicals according to the invention on each plant. In addition, the sucker control mixture may contain a surfactant and an emulsifying agent. The preceding ingredients are usually made up in a working solution which can be diluted with water by the user just prior to treatment to prepare an appropriate concentration for the particular crop to be treated.

The saturated fatty alcohols found to be useful in the homogeneous mixtures of the present invention include those in the range $C_6$ to $C_{18}$, although $C_8$ (octanol) and $C_{10}$ (decanol) alcohol and mixtures thereof are preferred. The $C_{10}$ alcohol has been found to give especially good results. Satisfactory sucker control can also be achieved by using a mixture of two or more saturated $C_6$–$C_{18}$ fatty alcohols in conjunction with the maleic hydrazide salt. The range of alcoholic mixtures which will provide satisfactory performance at the reduced levels of chemical application used in the present single treatment procedure is not limited to any particular critical range and almost any combination of saturated $C_6$–$C_{18}$ fatty alcohols may be employed. Among the fatty alcohol mixtures which can be successfully employed in the sucker control solutions of the invention are those enumerated in Schedule A.

SCHEDULE A

A - 99% (n-octanol), 1.0% $C_{10}$ (n-decanol).

B - 97% $C_{10}$ (n-decanol), 1.7% $C_8$ (n-octanol), 1.3% $C_{12}$ (n-dodecanol).

C - 97% (n-dodecanol), 2% $C_{14}$ (n-tetradecanol), 1% $C_{10}$(n-decanol).

D - 0.6% $C_6$ (hexanol), 43% $C_8$ (n-octanol), 56% $C_{10}$ (n-decanol), 0.4% $C_{12}$ (n-dodecanol).

E - 55% $C_{12}$ (n-dodecanol), 21% $C_{14}$ (n-tetradecanol), 10% $C_8$ (n-octanol), 8% $C_{10}$ (n-decanol), 5% $C_{16}$ (hexadecanol), 1% $C_6$ (N-hexanol).

F - 40% $C_{12}$ (dodecanol), 28% $C_{14}$ (n-tetradecanol), 15% $C_{16}$ (n-hexadecanol), 7% $C_8$ (n-octanol), 6% $C_{10}$ (n-decanol), 3% $C_{18}$ (n-octadecanol), 1% $C_6$ (n-hexanol).

G - 54% $C_8$ (n-octanol), 40% $C_{10}$ (n-decanol), 4% $C_6$ (n-hexanol), 1% $C_{12}$ (dodecanol), 1% $C_{14}$ (n-tetradecanol).

The maleic hydrazide derivatives found to be especially useful in the invention are the salts of 1,2-dihydropyridazine-3,6-dione. The potassium and diethanolamine salts have been found to give especially good results. Although the preceding dione composition is only slightly soluble in water at room temperature, the alkaline salts (e.g. potassium) may be easily formed by dissolving 1,2-dihydropyridazine-3,6-dione in an aqueous solution containing one equivalent, or an excess of the alkali. The salts which may be formed in this manner and are useful in the present invention include the alkali metal salts (e.g. potassium—from potassium hydroxide), ammonia and amines, such as alkylamines (e.g. the methylamine, dimethylamine, ethylamine, isopropylamine, dodecylamine, cyclohexylamine, and alkanolamine salts, for example ethanolamine, diethanolamine and triethanolamine derivatives). The alkali salts are more water soluble than the compound from which they are derived.

The salts may be easily prepared as follows. A thirty percent aqueous solution of the diethanolamine and triethanolamine salt of 1,2-dihydropyridazine-3,6-dione is prepared by adding equimolar ratios of the reactants to water to give 30% solutions. An aliquot of each solution is evaporated to dryness by heating at 100°–110° C. The resultant viscous oil is a diethanolamine salt, while the triethanolamine salt forms a partially crystalline mush.

Since the aqueous homogenized mixture of the invention is desirably applied in the form of an emulsion, it is preferably applied in admixture with a minor amount of a surface active wetting agent. Amoung the surface active agents found to be useful in the invention are those classified as anionic, non-ionic, and cationic surfactants. Specific anionic surfactants found to be useful include the sulfated or sulfonated ethers of long and short chain aliphatic groups (e.g. $C_{17}H_{33}$—O—$C_2H_4$—$SO_3$—Na), or $C_{17}H_{33}$—O—$C_2H_4$—O—$SO_3$—Na) sulfonated alkylesters of long chain fatty acids $$(C_{17}H_{33}-\overset{\overset{\displaystyle O}{\|}}{C}O-C_2H_4-SO_3-Na).$$

sulfonated glycol esters of long chain fatty acids $$(C_{17}H_{33}-\overset{\overset{\displaystyle O}{\|}}{C}O-C_2H_4-O-SO_3-Na).$$

sulfonated alkyl substituted amids of long chain fatty acids $$(\text{e.g. } C_{17}H_{33}-\overset{\overset{\displaystyle O}{\|}}{C}-NH-C_2H_4-SO_3Na).$$

alkylated aryl sulfonates (dodecyl benzene sodium sulfonate), hydroaromatic sulfonates (tetrahydronaphthalene sodium sulfonate), and alkyl sulfosuccinates (dioctyl sodium sulfosuccinate), alkyl sulfonates (e.g. dodecyl sodium sulfonate), alkyl sulfates (sodium oleyl sulfate), and soaps such as sodium laurate, ammonium stearate and diethanol-ammonium oleate). Useful nonionic surface active agents include monoethers of polyglycol with long chain fatty alcohols such as the reaction products of ethylene oxide or polyethylene glycol with long chain fatty alcohol, monesters of polyglycols with long chain fatty acids, including reaction products of ethylene oxide or polyethylene glycol with long chain fatty acids, partial esters of polyhydric alcohols with long chain monocarboxylic acids (glycerol monostearate, sorbitan trioleate), and partial and complete esters of long chain monocarboxylic fatty (and/or resinous) acids with polyglycol ethers or polyhydric alcohols (e.g. tristearate acid ester of polyglycol ether of sorbitan). Cationic surfactants useful in the invention include quaternary ammonium salts in which one of the groups attached to the nitrogen has an aliphatic group having at least 8 carbon atoms (e.g., trimethylacetylamoniumhalide). The foregoing are only meant to be exemplary of the wide range of surfactants which may be employed in the invention. An especially preferred surfactant for use in the present invention is available as Tween 20 (Atlas Chemical trademark for polyoxyethylene sorbitan monolaurate). The sucker control solutions of the present invention usually include from about 1 to about 5% by weight of surfactant.

In order to insure the formation of a suitable emulsion, an emulsifying agent such as Tween 80 (Atlas Chemical trademark for polyoxyethylene sorbitan-monooleate-specific gravity 1.00 through 1.05), a polyoxy alkylene derivative of hexitol anhydride partial long chain fatty acid ester, or Duponol-C (Du Pont Trademark) may be employed. Preferably between about 7 and 15% by weight of aqueous emulsifying agent is required to assure satisfactory emulsion properties in the mixture.

The saturated fatty alcohol, pyridazine salt, surfactant and emulsifier are combined and thoroughly admixed in water to make a stock homogenous solution which can be diluted to the desired working concentration, just prior to use.

EXAMPLES

Operation of the invention will be illustrated with typical formulations for tobacco sucker control agents according to the present invention as shown in Examples I and II below.

| Preferred Range of % | Especially Preferred Percent by weight | Composition |
|---|---|---|
| 9-12 | 11.0% | Potassium salt of 1,2-dihydro-3,6-pyridazine-dione |
| 1-5 | 3.0% | Tween 20 (surfactant) |
| 20-40 | 30.0% | N-decaol (B from Schedule A) |
| 7-15 | 11.0% | emulsifier (Tween 80 or Emsorb 6900) |
| To make 100% | | water |

EXAMPLE II

| Preferred Range of % | Especially Preferred Percent by Weight | Composition |
|---|---|---|
| 9-12 | 11.0% | Potassium salt of 1,2-Dihydro-pyridazine-3,6-dione |
| 1-5 | 3.0% | Tween 20 (surfactant) |
| 20-40 | 30.0% | 0.5%-$C_6$(hexanol)<br>43% - $C_8$ (n-octanol)<br>56% - $C_{10}$ n-decaol)<br>0.5% - $C_{12}$ (n-dodecanol) |
| 7-15 | 11.0% | Tween 80 |
| To make 100% | | water |

Diethanolamine salt may be substituted for the potassium salt of Examples I and II in a 10-15% preferred range, especially preferred percent by weight of 13%, of diethanolamine salt, this being the aliquot proportion of the active ingredient to the potassium salt.

Homogeneous solutions of the invention may be prepared by admixing the ingredients together in a suitable mixer of the propeller or impeller type at about 20° C. until an essentially homogeneous solution has been achieved. This will ordinarily require a mixing time anywhere from about 5 to about 50 minutes, depending upon the specific ingredients, quantities and type of mixing equipment employed.

When applied at the rate of approximately 6 to 12 quarts per acre on tobacco plants (approximately 6000 to 8000 plants per acre—approximately 0.60 to 1.0 ccs of saturated $C_6$-$C_{18}$ fatty alcohol per plant and from about 70 to about 125 milligrams per plant of 1,2-dihydropyridazine-3,6-dione salt per plant) within about a day after the plants have been topped, the compositions shown in Tables I and II will effectively control sucker growth with a single application. The aqueous mixture may be applied directly to the plants by tractor, or animal-drawn sprayer or by means of compressed air shoulder sprayer. A semi coarse spray is preferably employed and one or more rows are sprayed at a time, wetting only the upper one-third to one-half of the tobacco plant and allowing the liquid to run down the stalk of each plant.

Heretofore, when saturated $C_6$-$C_{18}$ fatty alcohols have been used by themselves as the sole sucker-control agents or in a sequential treatment scheme with maleic hydrazide, at least about 1.25 cc per plant of saturated fatty alcohols was required to provide acceptable results. Similarly, when maleic hydrazide is used as the sole sucker-control agent or as a sequential treatment following prior application of saturated fatty alcohols at least about 170 mgm per plant of the maleic hydrazide in the form of a salt in solution must be employed to achieve satisfactory sucker inhibition in the harvested plant. Thus, the minimum effective amount for achieving sucker inhibition in tobacco plants when either of the preceding constituents is applied alone as the sucker control agent or when they are applied in sequence, one after the other, is about 1.25 cc per plant of saturated $C_6$ through $C_{18}$ fatty alcohols and/or about 170 mgm per plant of maleic hydrazide (i.e. at least about 1.25 cc per plant of fatty alcohol and at least about 170 mgm per plant of maleic hydrazide). An important benefit achieved with the present invention is a substantial reduction in the level of chemicals required to effectively inhibit tobacco sucker growth and proliferation. In this respect, it has been found that by admixing the pyridazine salt and saturated $C_6$-$C_{18}$ fatty alcohol composition into a homogeneous aqueous solution and applying the solution to the tobacco plants within about a day after topping (the solution containing about 0.60-1.0 cc per plant of saturated $C_6$ through $C_{18}$ fatty alcohols and from about 70 to about 125 mgm per plant of maleic hydrazide in the form of the pyridazine salts described herein) equivalent or superior sucker inhibition is obtained with a single application of sucker control chemicals, as compared to the results which are achieved with plural applications of substantially larger amounts of either of the foregoing ingredients, alone or in separate sequential treatments. Accordingly, the solutions of the invention are formulated to provide from about 0.60 to about 1.0 cc per plant of saturated $C_6$-$C_{18}$ fatty alcohols and from about 70 to about 125 mgm per plant of 1,2-dihydro-pyridazine-3,6-dione salt. Experimental applications have established that the combined solutions of the invention provide satisfactory sucker-control on Burley tobaccos at levels approximately equal to one-half of the effective amount for controlling sucker proliferation of maleic hydrazide or saturated fatty alcohols, when these agents are used alone, or in sequential treatments.

Evaluations done on harvested flue-cured tobaccos establish that a single application of the pyridazine salt-saturated fatty alcohol solutions described herein, in which the alcohol and salt constituents are each present in an amount which is about two-thirds of their effective amount for inhibiting sucker growth when they are separately applied, provides equivalent or better sucker inhibition in harvested tobacco plants. In other words, a single administration of the combined maleic hydrazide derived salt and saturated $C_6$-$C_{18}$ fatty alcohol solutions of the present invention, using an amount per plant of each respective sucker inhibition constituent which is substantially less than the amount which would be required if the constituents were applied singly or in sequential treatments (i.e., alcohol followed in several days by maleic hydrazide or vice versa) provides equivalent or better control of tobacco suckers at harvest.

The following examples illustrate that a single treatment with the combined solutions of the present invention provides improved tobacco sucker control when compared to separate application of the same inhibition agents.

EXAMPLE III

Five gallons of a stock formulation as described in the preferred column of Table I was prepared and labeled Solution AB. Nine quarts of solution AB were drawn off and diluted to 50 gallons with water to make a working spray in the form of an aqueous emulsion. The fifty gallons of working spray was used to treat an acre containing about 8,000 topped tobacco plants once. In all instances the working solution was sprayed onto the upper section of the topped plant and the solution permitted to flow down along the main stem of the plant. The results of using this solution on Burley tobacco and a comparison with conventional treatments with potassium salt of 1,2-dihydro-pyridazine-3,6-dione and saturated fatty alcohol inhibitors alone, are shown in Table I below.

TABLE I

Sucker Control - Burley
Glade Spring, Va.
1974

Data are averages of four replications (8,000 plants/acre)

| Treatment Code | Suckers: Sucker Control % | Sucker Green Wt/ Plant gms. | Sucker/ Plant No. | Green Wt/ Sucker gms. |
|---|---|---|---|---|
| TNS[1] | 0 | 398 | 6.2 | 64.2 |
| HS[2] | 64 | 143 | 7.4 | 19.3 |
| D[3] | 83 | 67 | 2.6 | 25.8 |
| MH-30[4] | 91 | 34 | 1.6 | 21.2 |
| AB at 9 qts/A[5] | 99 | 4 | .3 | 13.3 |

Variety - Burley 21 planted May 24 and harvested Sept. 11.
Treated - Tobacco topped and treated Aug. 12
[1]Topped not suckered - no chemicals applied
[2]Hand suckered - no chemicals applied
[3]Fatty alcohol composition D from SCHEDULE A herein. 1.25 cc of fatty alcohol formulation applied per plant.
[4]Standard maleic hydrazide (MH) formulation-diethanolamine salt of 1,2-dihydropyridazine-3,6-dione. 170 mgm (MH)* applied per plant.
[5]73.5 mgm. as potassium salt of 1,2-dihydro-pyridazine-3,6-dione applied per plant and 0.60 cc. of fatty alcohol formulation B from Schedule A herein applied per plant - one application

EXAMPLE IV

Twelve quarts of a stock solution AB as in the preferred column of Table II were prepared and diluted to 50 gallons with water to make working solution AB. Working solution AB was sprayed at the rate of 50 gallons per acre on flue-cured tobacco (6,500 plants per acre) grown at Blackstone, Va., 1974 in a single application.

A different portion of the same crop was treated by spraying with conventional chemicals in sequential treatments. The results of sucker-inhibition measurements on all treated plants at harvest are shown in Table II below.

TABLE II

| Treatment | (Avg. of 3 Replications) No. of Suckers | Total Wt. of Suckers in Grams | Control % | Wt. Per Sucker (grams) |
|---|---|---|---|---|
| HS[1] | 66.3 | 1703 | — | 25.7 |
| Mixture of $C_8$ (n-octanol) and $C_{10}$(n-decanol) 2 separate sequential applns.[2] | 24.7 | 1121 | 34.2 | 45.4 |

TABLE II-continued

| Treatment | No. of Suckers | Total Wt. of Suckers in Grams | Control % | Wt. Per Sucker (grams) |
|---|---|---|---|---|
| Mixture of $C_8$ (n-octanol) and $C_{10}$ (n-decanol) followed in 7 days of diethanolamine salt of 1,2-dihydro-pyridarine-3,6-dione[3] | 20.3 | 361 | 78.8 | 17.8 |
| Working AB-12 qts./Acre, 1 appln.[4] | 3.0 | 27 | 98.4 | 9.0 |

[1]Hand suckered - no chemicals applied
[2]Total of 2.50 cc., applied per plant in two separate treatments of 1.25 cc. per plant at seven day interval
[3]1.25 cc mixture of $C_8$(n-octanol) and $C_{10}$(n-decanol) fatty alcohol emulsion D in Schedule A applied per plant followed by an application of 170 in the form of the diethanolamine salt of 1,2-dihydro-pyridazine-3,6-dione applied per plant in separate applications 7 days apart
[4]110.3 mgm as the potassium salt of 1,2-dihydro-pyridazine-3,6-dione applied per plant and 0.90 cc of fatty alcohol formulation applied per plant in a single combined solution sprayed on same day of treatment as 2 and 3 above.

EXAMPLE V

The following test was conducted to illustrate that the present invention results in a substantial reduction in the level of maleic hydrazide residues while simultaneously accomplishing effective sucker control as contrasted with the conventional maleic hydrazide treatment. The following Table illustrates the results of sucker inhibition and maleic hydrazide residue measurements made on treated plants at harvest.

TABLE III

| A - Burley Tobacco Grown in 4 Locations (Virginia, No. Carolina, Tenn. and Kentucky) | % Sucker Control | PPM-MH Residue |
|---|---|---|
| TNS[1] | 0 | 0 |
| H.S.[2] | 67.8 | 0 |
| MH[3] | 97.7 | 103.6 |
| AB[4] | 98.3 | 21.96 |

| B-Flue-Cured Tobacco Grown in 4 Locations (Georgia Virginia, No. Carolina (2)) | % Sucker Control | PPM-MH Residue |
|---|---|---|
| TNS[1] | 0 | 0 |
| HS[2] | 49.5 | 0 |
| FA/MH[5] sequential | 94.25 | 136.47 |
| AB[6] | 89.0 | 51.27 |

[1]Topped not suckered - no chemicals applied
[2]Hand suckered - no chemicals applied
[3]Standard maleic hydrazide (MH) formulation-diethanolamine salt of 1,2-diethanolamine salt of 1,2-dihydro-pyradazine 3,6-dione 170 mgm applied per plant in a single application.
[4]73.5 mgm as potassium salt of 1,2-dihydro-pyradazine-3,6 dione applied per plant and 0.60 cc of fatty alcohol formulation B from Schedule A herein applied per plant in a single combined application.
[5]Mixture of $C_8$(N-octanol) and $C_{10}$(n-decanol) fatty alcohol emulsion D in Schedule A applied per plant followed by an application of 170 mgm in the form of the diethanolamine salt of 1,2-dihydro-pyridazine 3,6-dione applied per plant in separate applications 7 days apart.
[6]110.3 mgm as the potassium salt of 1,2-dihydro-pyridazine-3,6 dione applied per plant and 0.9 cc of fatty alcohol formulation B from schedule A herein applied per plant in a single combination solution.

The results in Table III-A illustrate that although maleic hydrazide and the formulation of the present invention both provided effective sucker control, the level of maleic hydrazide residue in the finished tobacco product was substantially lower with the formulation of the present invention. In the above instance approximately 56% less maleic hyrazide was applied with the present invention as contrasted with the conventional treatment. Under these circumstances it would normally be expected to achieve a decrease in maleic hydrazide residue on the same order of magnitude (approximately 56% less or 58 ppm). Instead, the maleic hydrazide residue in the finished tobacco was reduced to 21.96 ppm with the present invention approximately 40% of the amount that would ordinarily have been anticipated from such a reduction in the amount of MH applied.

Referring to Table III-B, the average maleic hydrazide residue on the flue-cured plants treated according to the present invention was 51.27 parts per million while tobacco treated with the quantity of maleic hydrazide heretofore employed for sucker control had a residue of 136.47 parts per million. Thus, although 35% less maleic hydrazide was applied with the formulation of the present invention (as contrasted with the conventional rate illustrated in treatment 5), the maleic hydrazide residue level was reduced to about 58% less than would have ordinarily been anticipated from a 35% reduction in the amount of MH applied to each plant.

From the foregoing it will be apparent that the method of this invention provides effective sucker control with a single treatment and inhibits sucker proliferation at levels of chemicals well below those previously known to be useful by the prior art. The method and agent of the present invention also provides an effective means for achieving sucker control with a low initial quantity of maleic hydrazide while reducing the level of undesirable maleic hydrazide residues in the final tobacco product. Moreover, the aqueous homogeneous compositions of this invention are effective in controlling sucker growth and proliferation on widely varying strains of tobacco including flue-cured, Burley type, Hicks, Cigar type and Connecticut Broadleaf. It will be appreciated that in those instances of intensive sucker pressure excellent results can be obtained with lower quantities of materials by using two or more applications of the sucker control solutions of this invention.

What is claimed is:

1. A method of inhibiting the growth of suckers in tobacco plants which comprises applying to said tobacco plants after topping an effective amount for inhibiting tobacco sucker growth of an aqueous solution containing from about 10 to about 40% by weight of a saturated $C_6$ to $C_{18}$ fatty alcohol and from about 5 to about 25% by weight of a member selected from the group consisting of the alkali metal, [alkanolamine] *alkylamine* containing up to 12 carbon atoms, and $C_2$–$C_6$ [alkylamine] *alkanolamine* salts of 1,2-dihydropyridazine-3,6-dione.

2. The method of claim 1 wherein said solution is applied in the form of an aqueous emulsion.

3. The method of claim 1 wherein said fatty alcohol is N-decanol.

4. The method of claim 1 wherein said fatty alcohol is N-octanol.

5. The method of claim 1 wherein said fatty alcohol constituent comprises a mixture consisting essentially of N-octanol and N-decanol.

6. The method of claim 1 wherein said dione salt comprises the potassium salt of 1,2-dihydropyridazine-3,6-dione.

7. The method of claim 1 wherein said dione salt comprises the diethanolamine salt of 1,2-dihydropyridazine-3,6-dione.

8. The method of claim 7 wherein said solution includes a surface active wetting agent.

9. The method of claim 1 wherein said solution includes an emulsifying agent.

10. A liquid composition for inhibiting the growth of tobacco suckers consisting essentially of an aqueous solution containing from about 10 to about 40% by weight of a saturated $C_6$ to $C_{18}$ fatty alcohol and from about 5 to 25% by weight of a member selected from the group consisting of the alkali metal, [alkanolamine] *alkylamine* containing up to 12 carbon atoms, and $C_2$–$C_6$ [alkylamine] *alkanolamine* salts of 1,2-dihydropyridazine-3,6-dione.

11. The liquid composition of claim 10 wherein said salt comprises the potassium salt of 1,2-dihydropyridazine-3,6-dione.

12. The liquid composition of claim 10 wherein said salt comprises the diethanolamine salt of 1,2-dihydropyridazine-3,6-dione.

13. The liquid composition of claim 10 wherein said saturated fatty alcohol comprises N-octanol.

14. The liquid composition of claim 10 wherein said saturated fatty alcohol comprises N-decanol.

15. The composition of claim 10 wherein said saturated fatty alcohol constituent comprises a mixture consisting essentially of N-octanol and N-decanol.

16. The composition of claim 15 further including an emulsifying agent.

17. A liquid composition for inhibiting the growth of tobacco suckers as recited in claim 10 further including a wetting agent.

* * * * *